US00PP21857P2

(12) United States Plant Patent
Egger

(10) Patent No.: US PP21,857 P2
(45) Date of Patent: Apr. 5, 2011

(54) ***HEUCHERA* PLANT NAMED 'SUGAR PLUM'**

(50) Latin Name: *Heuchera hybrid*
Varietal Denomination: Sugar Plum

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 53 days.

(21) Appl. No.: 12/653,601

(22) Filed: Dec. 14, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner* — Kent L Bell
(74) *Attorney, Agent, or Firm* — Klarquist Sparkman, LLP

(57) ABSTRACT

A new and distinct hybrid of *Heuchera* plant characterized by deep red purple to silver medium-large sized leaves, light pink flowers on short dark burgundy flowering stems, a medium large mounding habit, excellent vigor, and excellent tolerance to heat and humidity.

2 Drawing Sheets

Botanical denomination: *Heuchera* hybrid.
Variety designation: 'Sugar Plum'.

BACKGROUND OF THE INVENTION

The present invention relates to a new and distinct cultivar of *Heuchera* hybrid and given the cultivar name of 'Sugar Plum'. *Heuchera* is in the family *Saxifragaceae. Heuchera* 'Sugar Plum' originated from a planned breeding cross between *Heuchera* 806-1, a proprietary unreleased plant, as the seed parent, and *Heuchera* 838-2, a proprietary unreleased plant, as the pollen parent. Compared to the seed parent the new cultivar has darker foliage and a light rather than a heavy veil. Compared to the pollen parent the new cultivar has leaves that are more purple. Compared to *Heuchera* 'Plum Royale' (U.S. Plant Pat. No. 20,935), the new cultivar is larger in habit and leaf size and the new cultivar has leaves that are deep red purple in the spring to silver with purple highlights in summer through winter rather than summer red purple.

This new *Heuchera* is distinguished by:

1. deep red purple to silver medium-large sized leaves,
2. light pink flowers on short dark burgundy flowering stems,
3. a medium large mounding habit,
4. excellent vigor,
5. and excellent tolerance to heat and humidity.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a one-year-old container grown plant for *Heuchera* 'Sugar Plum' in May in Canby, Oreg.

FIG. 2 shows a one-year-old *Heuchera* 'Sugar Plum' plant in the ground in the garden in November in Canby, Oreg.

DETAILED PLANT DESCRIPTION

Figure 3:
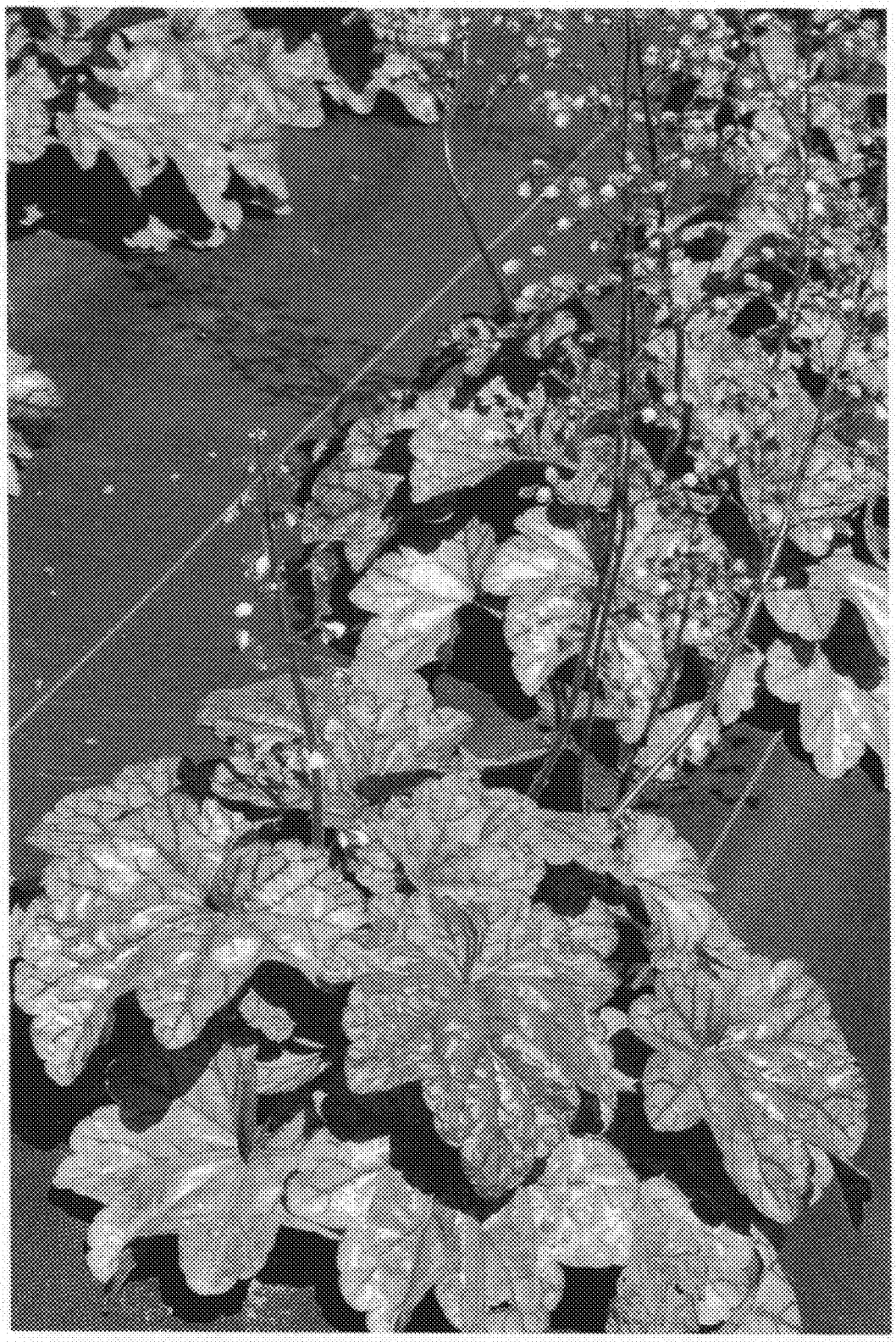
FIG. 3 shows nine-month plants of *Heuchera* 'Sugar Plum' growing in the ground in full sun in the trial field in May in Canby, Oreg.

The following is a detailed description of the new *Heuchera* cultivar based on observations taken in May of one-and-a-half-year-old specimens grown in the ground in a garden in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 5th edition.

Plant:

*Form.*—Basal rosette, herbaceous perennial.
*Hardiness.*—USDA Zone 4 to 9.
*Size.*—28 cm tall from top of the foliage to the ground and 46 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Rosette.
*Number of leaves.*—30 to 50.
*Shape.*—Broadly ovate to orbicular.
*Lobing/division.*—5 shallow lobes, each with secondary lobes, the terminal is the longest.
*Venation.*—Palmate.
*Margins.*—Crenate.
*Apex.*—Mucronulate.
*Base.*—Cordate, lobes overlapping slightly at the base.
*Blade size.*—Grows to 10.5 cm long and 10.5 cm wide.
*Surface texture.*—Glandular on both sides.
*Petiole description.*—12 cm to 16 cm long and 3 mm wide, glandular hairs, Purple N79A.

*Leaf color.*—Variable depending amount of light, temperature, and age of the leaf; spring topside Purple N79A with darker veins, bottom side blade and veins Greyed Purple N186A; summer through winter topside silver, Greyed Purple N187D, tinged purple, N79A, with dark margins and veins, Greyed Purple N187A, bottom side Greyed Purple N186C.

Inflorescence:

*Size.*—Grows to 24 cm long and 6.5 cm wide.

*Type.*—Thyrse.

*Number of flowers per thyrse.*—About 90 per thyrse.

*Number of thyrse.*—About 12 in first spring bloom.

*Peduncle.*—Grows to 22 cm tall, 3 mm wide at base, Greyed Purple N186C, glandular hairs, with 0 to 1 leaves (broadly ovate to orbicular, grows to 4 cm long and 4.5 cm wide, 5 to 7 lobed, broadly crenate, mucronulate, cordate, colored like summer leaves above).

*Pedicel.*—Variable in size, with glandular hairs, Greyed Purple N186C.

*Bloom period.*—May to August in Canby, Oreg.

Flower bud:

*Size.*—3 mm wide and 5 mm long.

*Description.*—Glandular puberulent, ovoid, down facing.

*Color.*—Yellow White 158B tinged with Red Purple 61C on top half and Red Purple 61C on bottom half darkening to Greyed Purple 183C on bottom quarter.

Flower:

*Type.*—Perfect.

*Shape.*—Campanulate.

*Size.*—6 mm long and 4 mm wide.

*Petal description.*—5 in number, inconspicuous, 3 mm long and 1 mm wide, spatulate, tip obtuse, margin entire, glabrous on top side, glandular on bottom; Red Purple 62D on both sides.

*Calyx description.*—Campanulate, 6 mm long and 4 mm wide, with 5 lobes, divided ⅓ way to the base, glandular hairs on both sides, obtuse, entire, White N155B tinged Red Purple 62B on top half and Greyed Purple 186B on bottom half.

*Stamen description.*—5 in number, filaments 3 mm long, White NN155C, anthers 0.5 mm, Orange 29A, pollen Orange 28A.

*Pistil description.*—1, 2-beaked, 5 mm long, Red Purple 62D overall, ovary 2 mm, style 3 mm long.

*Fragrance.*—None.

*Lastingness.*—Each thyrse blooms for about 2 weeks on the plant.

Fruit:

*Type.*—Two beaked capsules.

*Size.*—3.5 mm deep by 5 mm wide.

*Fertility.*—Good.

*Color.*—Brown 200D.

Seed:

*Shape.*—Linear.

*Size.*—2 mm long.

*Color.*—Black, 202A.

Pest and disease tolerance: Excellent disease resistance to powdery mildew, the common problem of *Heuchera.* Susceptible to *Heuchera* rust and root weevils.

I claim:

1. A new and distinct hybrid of *Heuchera* plant as herein illustrated and described.

* * * * *

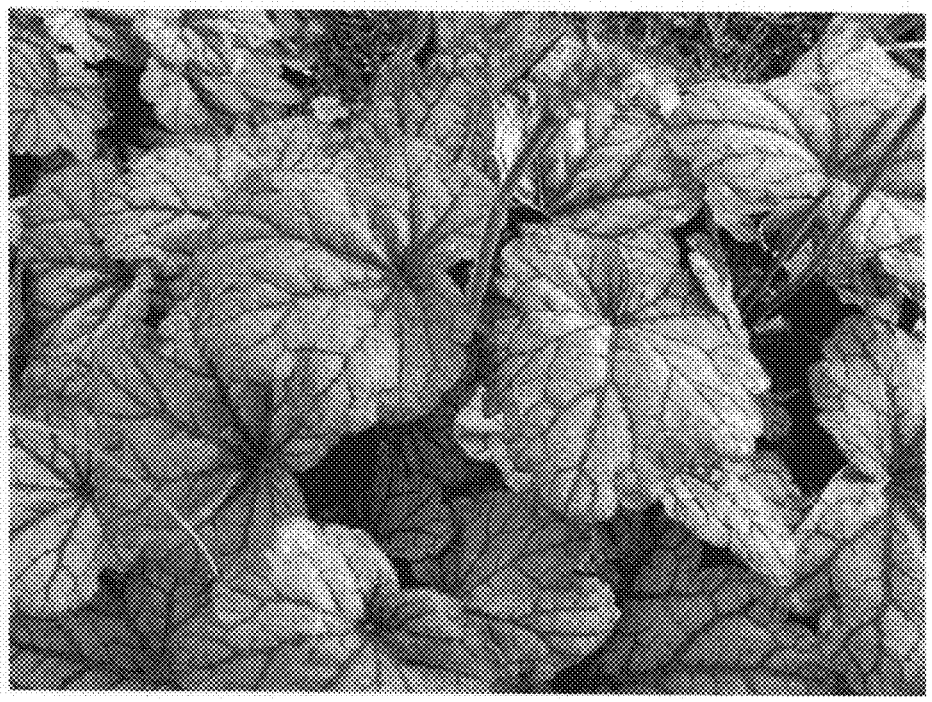

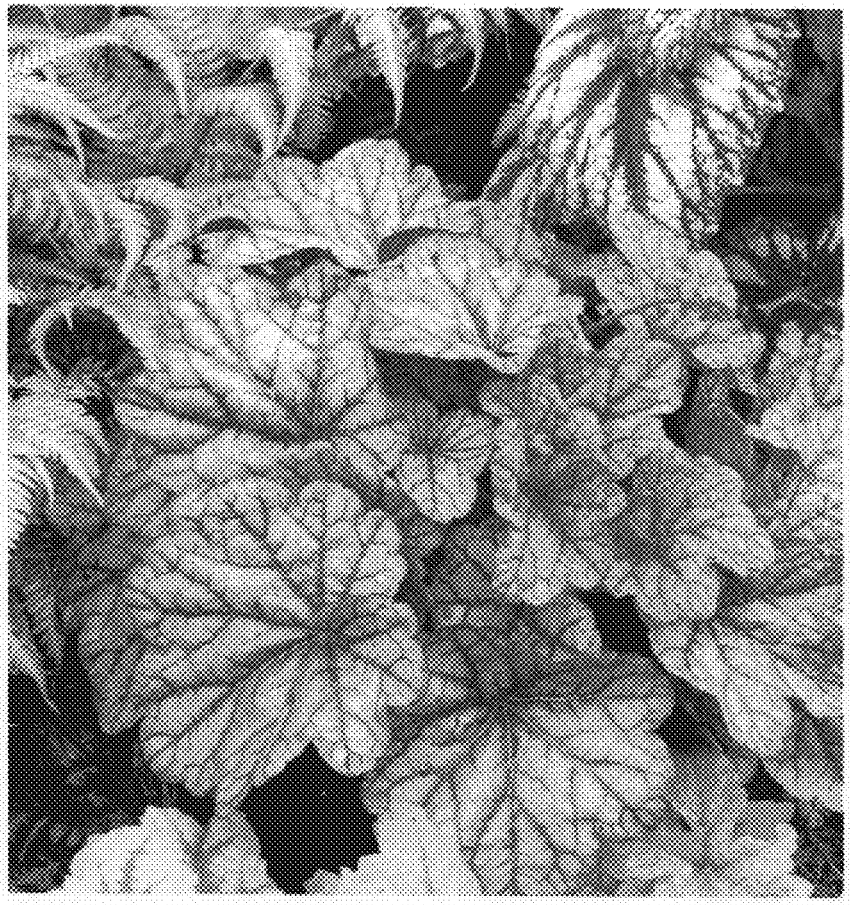
Figure 1 above, Figure 2 below